US00PP28664P2

(12) United States Plant Patent
Thompson

(10) Patent No.: US PP28,664 P2
(45) Date of Patent: Nov. 21, 2017

(54) JAPANESE HASKAP PLANT NAMED 'KAWAI'

(50) Latin Name: ***Lonicera caerulea* ssp. *emphyllocalyx***
Varietal Denomination: Kawai

(71) Applicant: Maxine M. Thompson, Corvallis, OR (US)

(72) Inventor: Maxine M. Thompson, Corvallis, OR (US)

(73) Assignee: MAXINE M. THOMPSON TRUST, Corvallis, OR (US)

( * ) Notice: Subject to any disclaimer, the term of this patent is extended or adjusted under 35 U.S.C. 154(b) by 43 days.

(21) Appl. No.: 14/757,023

(22) Filed: Nov. 9, 2015

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Keith Robinson
(74) *Attorney, Agent, or Firm* — Penny J. Aguirre

(57) ABSTRACT

A new cultivar of Japanese haskap plant, 'Kawai', that is characterized by its upright and spreading plant habit, its vigorous growth habit, its high fruit yields, its early mid-season fruit harvest, its fruit that are medium in size, ovate-rectangular in shape with a blunt concave apex, medium in firmness with a sweet/tart juice flavor, and its fruit attachment to the stem that is strong enough to prevent pre-harvest drop and loose enough to permit easy picking without tearing the fruit flesh.

2 Drawing Sheets

Botanical classification: *Lonicera caerulea* ssp. *emphyllocalyx*.

Variety denomination: 'Kawai'.

CROSS REFERENCE TO RELATED APPLICATIONS

This application is co-pending with U.S. Plant Patent Applications filed for plants derived from the same breeding program that are entitled Japanese haskap Plant Named 'Kapu' (U.S. Plant Pat. No. 26,820) and Japanese haskap Plant Named 'Keiko' (U.S. Plant Pat. No. 26,642).

BACKGROUND OF THE INVENTION

The present invention relates to a new and distinct cultivar of *Lonicera caerulea* ssp. *emphyllocalyx* and will be referred to hereafter by its cultivar name, 'Kawai'. 'Kawai' is a new cultivar of Japanese blue honeysuckle berry, also known as Japanese haskap, a plant grown for its fruit that is marketed as fresh fruit, frozen fruit and quality processed food products.

The new Invention arose from an ongoing controlled breeding program in Corvallis, Oreg. that commenced with the planting of seeds collected in 2000 from several berry farms in Hokkaido, Japan. The objectives of the breeding program are to develop superior cultivars of this early ripening berry plant that could be grown in moderate to colder climates combined with an upright spreading plant habit and fruit that were large in size, firm, easy to pick, good tasting, with a high yield rate and a harvest season that exhibits a range of fruit maturity.

This new Japanese haskap cultivar, 'Kawai', arose from a cross made from unnamed and unpatented Japanese haskap plants from the Inventor's breeding program in 2006 with the female parent designated as seedling No. 21-78 and the male parent designated as seedling No. 41-75. 'Kawai' was selected in Corvallis, Oreg. as a single unique plant, designated as seedling No. 108-42 in 2009 from the population of resulting seedlings from the above cross.

Asexual propagation of the new cultivar was first accomplished by the Inventor by hardwood stem cuttings in 2009 in Corvallis, Oreg. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors in a trial plot in Corvallis, Oreg. These attributes in combination distinguish 'Kawai' as a unique cultivar of Japanese haskap.

1. 'Kawai' exhibits an upright and spreading plant habit.
2. 'Kawai' exhibits a vigorous growth habit.
3. 'Kawai' exhibits high fruit yields.
4. 'Kawai' exhibits an early mid-season fruit harvest.
5. 'Kawai' exhibits fruit that are medium in size, ovate-rectangular in shape with a blunt concave apex, and medium firmness with a sweet/tart juice flavor.
6. 'Kawai' exhibits a fruit attachment to the stem that is strong enough to prevent pre-harvest drop and loose enough to permit easy picking without tearing the fruit flesh.

The female parent of 'Kawai', seedling No. 21-78, differs from 'Kawai' in having fruit that is smaller in size, matures one week earlier, and prone to pre-harvest drop. The male parent differs from 'Kawai' in having a more open growth habit and in having fruit that is oval-ovate in shape and a harvest date that is one week later. 'Kawai' can be most closely compared to Japanese haskap cultivars 'Kapu' and 'Keiko'. 'Kapu' is similar to 'Kawai' in having fruit with a sweet/tart flavor. 'Kapu' differs from 'Kawai' in having a more upright growth habit, in having fruit that is oval-ovate in shape, firmer, and matures two weeks later. 'Keiko' differs from 'Kawai' in having fruit with a more tart flavor, is oval in shape, and that matures 12 days later.

BRIEF DESCRIPTION OF THE DRAWINGS

The accompanying colored photographs were taken in mid summer and illustrate the overall appearance and distinct characteristics of 8 year-old plants of the new Japanese haskap as grown in a trial garden in Corvallis, Oreg.

The photograph in FIG. 1 provides a view of the plant habit of 'Kawai'.

Figure 1:
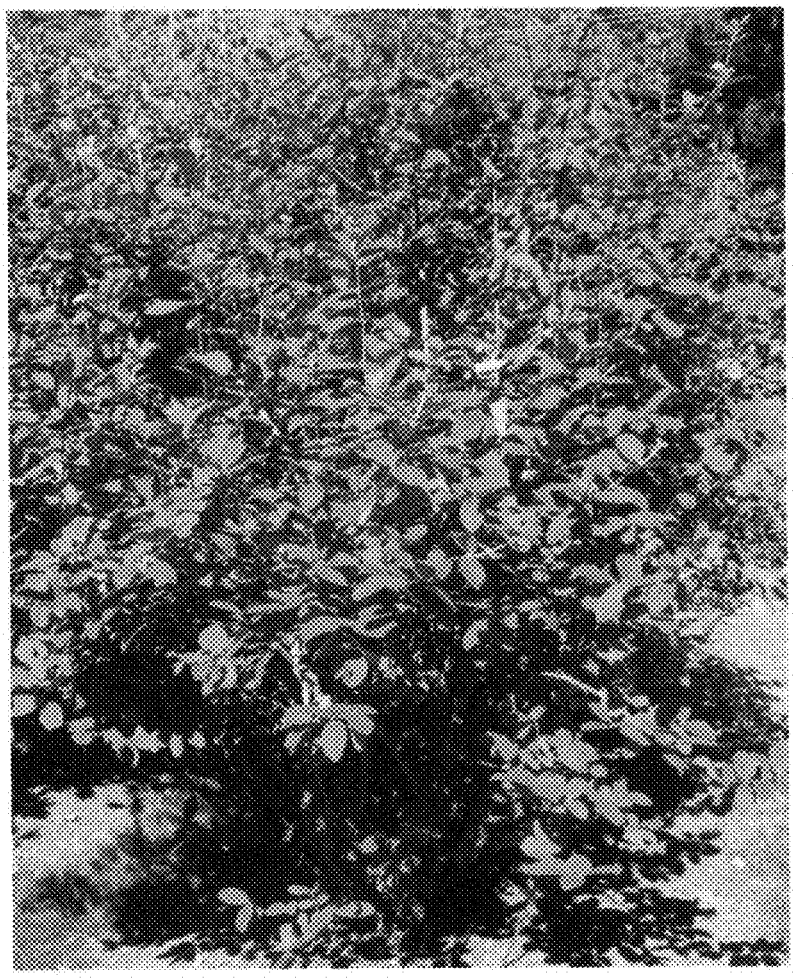
Figure 2:
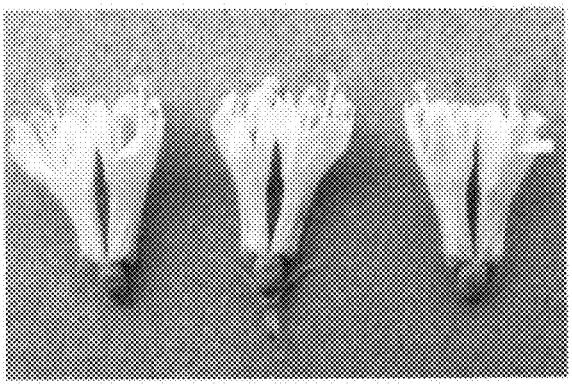

The photograph in FIG. 2 provides a close-up view of the flowers of 'Kawai'.

Figure 3:
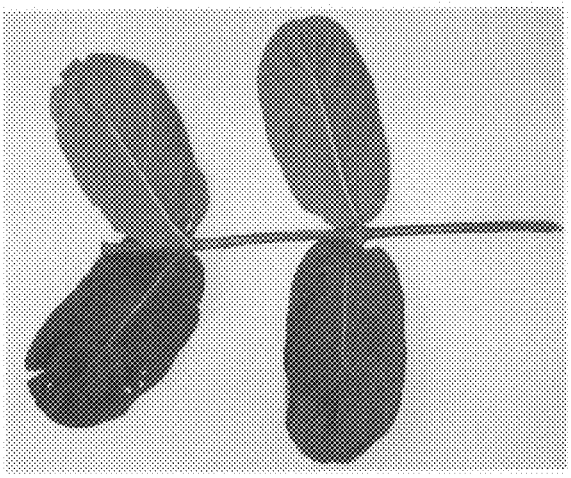

The photograph in FIG. 3 provides a close-up view of the leaves of 'Kawai'.

Figure 4:
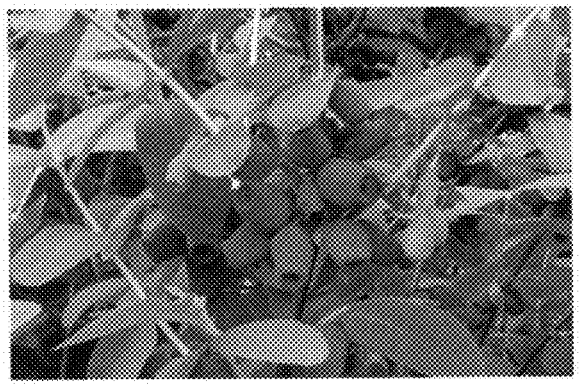

The photograph in FIG. 4 provides a view of the berries of 'Kawai'.

The colors in the photographs may differ slightly from the color values cited in the detailed botanical description, which accurately describe the colors of the new Japanese haskap.

DETAILED BOTANICAL DESCRIPTION

The following is a detailed description of 8 year-old plants of the new Japanese haskap as field grown at the Inventor's farm in Corvallis, Oreg. under irrigation. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Plant type*.—Deciduous shrub, fruit bearing.

*Plant habit*.—Upright and spreading.

*Plant size*.—Reaches an average of 1.75 m in height and 1.4 m in width.

*Hardiness*.—Adapted well in Zone 8b, expected to be hardy to U.S.D.A. Zone 4 but they have not been tested to date.

*Diseases and pests*.—No significant diseases or pest problems have been observed to date.

*Root description*.—Fibrous.

*Propagation*.—Softwood and hardwood stem cuttings.

*Growth rate*.—Vigorous.

*Root development*.—10 days to initiate roots in summer at 26° C., and 35 days to produce a fully rooted cutting or a young rooted plant in a liner at 26° C.

Dormant shoots:

*Density*.—Medium.

*New growth*.—145A in color, and glabrous surface.

*One year-old shoots*.—54 cm in length and 4 mm in diameter, surface is smooth and glabrous, lenticels absent, 165B in color, adventitious bud development; weak, dormant without pruning, average of 2 per node, up to 2.5 mm in length and 2 mm in width, ovate in shape, 164B in color.

*Three year-old stems*.—1.25 m in length and 1.2 cm in diameter, surface exfoliating, inner bark 177D in color, outer bark 197A in color.

*Bud break*.—Early March in Corvallis, Oreg.

Foliage description:

*Leaf shape*.—Oval.

*Leaf division*.—Simple.

*Leaf base*.—Rounded.

*Leaf apex*.—Obtuse.

*Leaf venation*.—Pinnate, color primarily matches leaf color on both surfaces.

*Leaf margins*.—Entire.

*Leaf arrangement*.—Opposite.

*Leaf attachment*.—Petiolate.

*Leaf surface*.—Young leaf and mature leaves, upper and lower surfaces are glabrous.

*Leaf internode length*.—An average of 6.5 cm.

*Leaf size*.—Average of 7.3 cm in length and 4.3 cm in width.

*Leaf color*.—Young leaves; upper surface 138A and lower surface 138B, mature leaves; upper surface 138A, lower surface 138B.

*Petioles*.—Up to 2 mm in length and 1 mm in width, 145C in color, glabrous surface.

*Stipules*.—Absent.

Inflorescence description:

*Blooming period*.—An average of 22 days, typically between March 29$^{th}$ and April 20$^{th}$ with mid bloom around April 9$^{th}$ in Corvallis, Oreg.

*Inflorescence type*.—Small 2-flowered cymule born in leaf axils of lowest 1 to 4 nodes on current years' growth.

*Inflorescence size*.—An average of 2.3 cm in length and 1.8 cm diameter.

*Flower buds*.—Mixed buds, flower buds are not visible as they are enclosed within the leaves.

*Flower fragrance*.—None.

*Lastingness of inflorescence*.—4 to 6 days.

*Flower quantity*.—2 to 6 per shoot.

*Flower type*.—Epigynous.

*Corolla form*.—Funnel form, narrow at the base and widening towards apex, 5-lobed.

*Flower size*.—Length from base of ovary to stigma is 2.3 cm; average of base width is 2 mm, average of apex is 8 mm.

*Peduncles*.—Up to 2 mm in length, 1 mm in diameter, 139C in color, glabrous surface.

*Pedicels*.—Inconspicuous.

*Bracts*.—2, present at the base of the ovaries, linear in shape, upper surface color is 139C, lower surface color is 139D, upper and lower surfaces are glabrous, cuspidate apex, cuneate base, 2 mm in width and 8 mm in length.

*Sepals*.—Fused with hypanthium, 4.5 mm in length.

*Petals*.—5, fused into tube with apex of each free forming lobes, 2 mm in width at the base, 1.5 mm in diameter at apex and tube is 1.4 cm in length, free portion length is 5 mm and 3 mm in width, acute in shape, color of inside and outside of tube is 18B, inner surface is glabrous, outer surface is pilose.

Reproductive organs:

*Gynoecium*.—1 pistil, an average of 2.3 cm in length, style is 1.8 cm in length and 18D in color, stigma is 1 mm in diameter and 18D in color, ovary is inferior, oval in shape, 4 mm in length, 3 mm in width and 139C in color.

*Androcoecium*.—5 stamens, adnate to inner corolla tube, filaments are 18B in color and about 8 mm in length, anthers are 18A in color, pollen is abundant in quantity and 18A in color with 100% acetocarmine stain.

*Compatibility*.—Self-incompatible.

Fruit description:

*Fruit development*.—59 days from mid-bloom to harvest.

*Harvest date*.—Average of June $7^{th}$ in Corvallis, Oreg.

*Fruit type*.—True berry, consists of 2 ovaries enclosed in the hypanthium.

*Fruit shape*.—Shape is ovate-rectangular with a blunt concave apex.

*Fruit size*.—An average of 1.9 cm in length and 1.5 cm in width.

*Fruit surface*.—Smooth with heavy bloom.

*Fruit apex*.—Flat with rolled edges.

*Fruit skin color*.—93A with bloom removed, 188B with bloom.

*Fruit flesh color*.—145A.

*Fruit firmness*.—Medium firm.

*Fruit brix*.—13°.

*Fruit juiciness*.—Small amount.

*Fruit weight*.—An average of 1.7 g.

*Fruit yield*.—3.6 kg per 8 year-old bush.

*Peduncle-berry scar*.—Very small, dry, up to 1.2 cm in length.

*Fruit attachment strength*.—Medium; strong enough to avoid pre-harvest drop and loose enough to pick without tearing berry flesh.

*Pre-harvest drop*.—Insignificant.

*Post-harvest*.—Berries maintain their appearance, firmness and taste for at least 3 weeks in cold storage at 33° F. to 35° F.

*Market uses*.—Fresh, frozen, dried, and particularly suited for processed products.

*Seed*.—Average of 18 seeds per fruit, lenticular in shape, dry weight size is 146 mg/100 seeds, 177C in color.

It is claimed:

1. A new and distinct cultivar of Japanese haskap plant named 'Kawai' as herein illustrated and described.

* * * * *